United States Patent
Saito et al.

(10) Patent No.: US 7,084,379 B2
(45) Date of Patent: Aug. 1, 2006

(54) CONTROL APPARATUS FOR GAS SENSOR

(75) Inventors: Takuya Saito, Aichi (JP); Takeshi Kawai, Aichi (JP); Satoshi Teramoto, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 11/082,902

(22) Filed: Mar. 18, 2005

(65) Prior Publication Data

US 2005/0205550 A1    Sep. 22, 2005

(30) Foreign Application Priority Data

Mar. 22, 2004  (JP) ............................ 2004-083737

(51) Int. Cl.
*H05B 1/02*    (2006.01)

(52) U.S. Cl. .................. 219/497; 219/202; 219/492; 374/132; 123/697

(58) Field of Classification Search .............. 219/497, 219/505, 492, 499, 507, 508, 202, 205; 123/672, 123/681, 695–699, 688, 676; 374/132, 141; 204/406, 424
See application file for complete search history.

(56) References Cited

U.S. PATENT DOCUMENTS

| | | | |
|---|---|---|---|
| 5,719,778 A | * | 2/1998 | Suzumura et al. .......... 700/207 |
| 6,304,812 B1 | | 10/2001 | Kolmanovsky et al. |
| 6,476,364 B1 | * | 11/2002 | Shimamura et al. ........ 219/494 |
| 2002/0000436 A1 | * | 1/2002 | Hashimoto et al. ......... 219/497 |
| 2003/0084892 A1 | * | 5/2003 | Ohkuma .................... 123/688 |
| 2005/0006368 A1 | * | 1/2005 | Sell et al. ................... 219/202 |

FOREIGN PATENT DOCUMENTS

JP    2001-41923    2/2001

* cited by examiner

*Primary Examiner*—Mark Paschall
(74) *Attorney, Agent, or Firm*—Sughrue Mion, PLLC

(57) ABSTRACT

A control apparatus for a gas sensor, wherein a microcomputer 44, which is connected to an oxygen sensor 30 including a detection element 12 and a heater 14, detects the cooling water temperature Tw of the engine. The control apparatus determines that condensation water within the exhaust pipe is being generated when the cooling water temperature Tw is equal to or lower than 0° C. When equal to or lower than 0° C., the microcomputer 44 supplies to the heater 14 electrical power for maintaining the temperature of the detection element 12 within the range of 100° C. to a splash-water-cracking generation temperature (e.g., about 300° C.) at or above which cracking can occur in a laminated-type oxygen sensor element 10 due to splash of condensation water. Electrical power is supplied to the heater 14 such that a pulse signal Sh is output from the microcomputer 44, and the heater 14 is pulse-driven by use of a heater electrification control circuit 34.

7 Claims, 5 Drawing Sheets

CONTROL APPARATUS FOR GAS SENSOR

BACKGROUND OF THE INVENTION

1. Field of the Invention

The present invention relates to a control apparatus equipped with a gas sensor which is used, for example, for controlling an air-fuel ratio of an internal combustion engine.

2. Description of the Related Art

In general, a gas sensor including a gas element is disposed in an exhaust system of an internal combustion engine for use in controlling the engine's air-fuel ratio. A widely known type of gas sensor element includes a detection element constituted by an oxygen-ion conductive solid electrolyte (e.g., zirconia) and electrodes formed on the surface thereof, and a heater for heating the detection element to an activation temperature or higher temperature. The heater generates heat when electrical power is supplied thereto from an external power source, and its heat generation quantity can be controlled by controlling the supply of electricity to the heater.

In order to accurately detect a specific gas, electricity is desirably supplied to the heater in such manner that the temperature of the detection element is rapidly increased, to thereby quickly activate the gas detection section of the detection element. However, under conditions where the temperature of the interior of the exhaust pipe (the temperature of the wall surface of the exhaust pipe) is low (e.g., at the time of cold start of the engine) and moisture contained in exhaust gas discharged from the engine condenses within the exhaust pipe; that is, under conditions where condensate is produced within the exhaust pipe, and when the detection element is heated to a high temperature by supplying electricity to the heater, a phenomenon called "splash water cracking" may occur. That is, the gas sensor element may crack due to thermal shock when condensation water adheres to the gas sensor element to quickly cool the same.

In view of the above, in order to suppress splash water cracking of a gas sensor element, a technique has been proposed for determining, using a temperature detection means attached to the wall surface of the exhaust pipe, whether or not water is present within the exhaust pipe, and limiting the supply of electricity to the heater when water is detected within the exhaust pipe (see, for example, Patent Document 1). In this technique, when it is determined that condensation water is being generated within the exhaust pipe, the supply of electricity to the heater is restricted so as to mitigate thermal shock imparted to the gas sensor element when condensation water adheres to the gas sensor element. When it is determined that condensation water is not being generated within the exhaust pipe, the restriction on the supply of electricity to the heater is removed, and main electrification is begun in order to activate the detection element.

[Patent Document 1] Japanese Patent Application Laid-Open No. 2001-41923.

3. Problems to be Solved by the Invention

However, through studies performed by the present inventors, it was found that the phenomenon of cracking of a gas sensor element cracking is observed not only in the case where condensation water adheres to the gas sensor element while being heated to high temperature, whereby the gas sensor element is subjected to thermal shock resulting in splash water cracking, but also in the case where water has adhered to the detection element before start of supply of electricity to the heater or where condensation water adheres to a detection element which has been heated to a temperature of less than 100° C. (hereinafter referred to as "condensation water cracking").

That is, at the time of cold start of the internal combustion engine, the gas sensor element itself is cold, and condensation water may adhere to the outer surface of the detection element from the beginning of cold start. When supply of electricity to the heater is commenced in this state, the temperature of the heater increases continuously. However, because of the condensation water adhering to the surface of the detection element, the temperature of the detection element does not increase beyond about 100° C. until the condensation water evaporates. If there is a large difference in temperature between the heater and the detection element, at the instant when the condensation water adhering to the surface of the detection element has completely evaporated, the temperature of the detection element abruptly increases. This is due to influence of the heater, whereby cracking (condensation water cracking) may be generated in the detection element due to thermal shock.

The technique of the above-mentioned Patent Document 1 restricts supply of electricity to the heater when it is determined that condensation water is being generated within the exhaust pipe. However, Patent Document 1 does not describe the temperature at the time when restriction on the supply of electricity to the heater is removed. Therefore, according to this technique, supply of electricity to the heater may be restricted in such manner that the temperature of the detection element is maintained in a region below 100° C. However, in some cases the above-described condensation water cracking is induced when the mode of supply of electricity to the heater is switched to main electrification after having been restricted to maintaining the temperature of the detection element below 100° C. Specifically, in the case where water adheres to the surface of the detection element before start of supply of electricity to the heater, the above-described heater control causes the following phenomenon. Although the temperature of the heater increases continuously after the start of main electrification, the temperature of the detection element does not quickly elevate and exceed 100° C., with resultant occurrence of condensation water cracking.

SUMMARY OF THE INVENTION

The present invention has been accomplished in view of the above-mentioned problems of the prior art, and an object of the present invention is to provide a control apparatus for a gas sensor which can suppress not only splash water cracking of a detection element, but also condensation water cracking thereof at the time of cold start of an internal combustion engine.

The above object has been achieved by providing a control apparatus for a gas sensor, which apparatus is connected to a gas sensor element which includes a detection element capable of detecting a specific gas contained in exhaust gas passing through an exhaust pipe of an internal combustion engine and a heater for heating the detection element. The control apparatus comprises heater electrification means for supplying electricity to the heater such that the detection element is heated to an activation temperature or higher temperature. The control apparatus further comprises condensation water determination means for determining whether condensation water within the exhaust pipe is being generated; and pre-electrification means for supplying electricity to the heater, in place of the heater electrification means, when the condensation water determination means determines that condensation water within the exhaust pipe is being generated. The pre-electrification means supplies to the heater electrical power for maintaining the temperature of the detection element within a temperature range of not lower than 100° C. but below a splash-water-cracking generation temperature at or above which the gas sensor element is subject to cracking when splashed with condensation water.

A characteristic feature of the control apparatus for a gas sensor of the present invention resides in that when the condensation water determination means determines that condensation water within the exhaust pipe is being generated, the pre-electrification means supplies to the heater electrical power for maintaining the temperature of the detection element within a temperature range of not lower than 100° C. but below the splash-water-cracking generation temperature.

As described above, in the present invention, when it is determined that condensation water within the exhaust pipe is being generated, using the pre-electrification means, electrical power is supplied to the heater so as to render the temperature of the detection element equal to or higher than 100° C. Therefore, even in the case where condensation water adheres to the surface of the detection element from the beginning of cold start of the internal combustion engine, or when condensation water adheres to the surface of the detection element immediately after the cold start, evaporation of such condensation water is accelerated during pre-electrification. Further, the pre-electrification means supplies electrical power to the heater for maintaining the temperature of the detection element within a range below the splash-water-cracking generation temperature, while rendering the temperature of the detection element equal to or higher than 100° C. Therefore, even when condensation water adhering to the detection element evaporates during pre-electrification, the temperature difference between the detection element and the heater can be suppressed to a small level, whereby generation of condensation water cracking during pre-electrification can be prevented.

Moreover, since the pre-electrification means supplies to the heater electrical power for maintaining the temperature of the detection element within the range below the splash-water-cracking generation temperature, splash water cracking can be suppressed, which would otherwise occur when a droplet of condensation water airborn within the exhaust pipe contacts the gas sensor element. In the present specification, the splash-water-cracking generation temperature means "a temperature at which a crack is generated in a gas sensor element when a water droplet of 2 µl is dropped on the outer surface of the gas sensor element during a period in which the temperature of the detection element is gradually elevated by continuous application of a constant DC voltage to the heater." The temperature of the detection element can be measured by means of a thermocouple disposed on a gas detection section of the detection element, which section is to be exposed to exhaust gas. Specifically, the splash-water-cracking generation temperature is set to fall within a range not lower than 250° C. but lower than 350° C.; more preferably, a range not lower than 250° C. but not higher than 300° C., in order to suppress splash water cracking without fail.

Notably, in the present invention, no particular limitation is imposed on the manner of providing the heater insofar as the heater is disposed near the detection element. For example, when the detection element is formed in the shape of a bottomed cylinder, the heater may be inserted into the interior of the detection element. When the detection element is formed in the shape of a plate extending along the longitudinal direction, the heater may be laminated on the detection element. Notably, in the case where the heater is laminated on the plate-shaped detection element, the detection element and the heater may be fired as a unitary member, or the detection element and the heater may be bonded together via a bonding layer. In particular, a gas sensor element having a structure in which a plate-shaped detection element and a plate-shaped heater are laminated can be made compact as compared with the case of a cylindrical gas sensor element (detection element), and during pre-electrification, can considerably accelerate the evaporation of condensation water adhering to the detection element. Therefore, a gas sensor element used for the gas sensor control apparatus of the present invention preferably has a structure in which a plate-shaped detection element and heater are layered. A well-known power control method may be used for supplying electrical power (predetermined electrical power) to the heater using pre-electrification means or heater electrification means. An example of the known power control method includes PWM (pulse width modulation) control.

In the above-described control apparatus for a gas sensor, the condensation water determination means preferably determines whether condensation water within the exhaust pipe is generated, on the basis of temperature of cooling water of the internal combustion engine. Because the cooling water temperature is strongly correlated with the wall temperature of the exhaust pipe, such determination can be performed accurately in a simple manner.

Moreover, in the above-described control apparatus for a gas sensor, the pre-electrification means preferably supplies electrical power to the heater at a first power level during a predetermined period of time after the condensation water determination means determines that condensation water within the exhaust pipe is generated, and supplies electrical power to the heater at a second power level lower than the first power level after passage of the predetermined period of time.

Condensation water cracking may occur not only when condensation water adheres to the detection element before startup of the internal combustion engine, but also when a droplet of condensation water flying within the exhaust pipe adheres to the detection element after start of supply of electricity to the heater but before the temperature of the detection element reaches 100° C. In view of the above, in the present invention, during a predetermined period of time after condensation water is determined to be generated, electrical power at a relatively high first power level is supplied to the heater so as to cause the temperature of the detection element to quickly reach 100° C. After that, electrical power at a second power level lower than the first power level is supplied to the heater. With this operation, condensation water cracking of the detection element at the time of cold start of the internal combustion engine can be prevented more reliably.

Moreover, in the above-described control apparatus for a gas sensor, the pre-electrification means preferably calculates, on the basis of a voltage value of the power source voltage, a duty ratio of the voltage waveform applied to the heater, and controls supply of electricity to the heater by pulse width modulation (PWM) to thereby supply electrical power to the heater at the first and second power levels. PWM control is advantageous in that the power supplied to the heater can be easily adjusted by controlling its duty ratio. Therefore, during pre-electrification, through PWM control of supply of electrical power at the first and second power levels, supply of electricity to the heater can be accurately controlled without use of a complex control method.

DESCRIPTION OF REFERENCE NUMERALS

Figure 1:
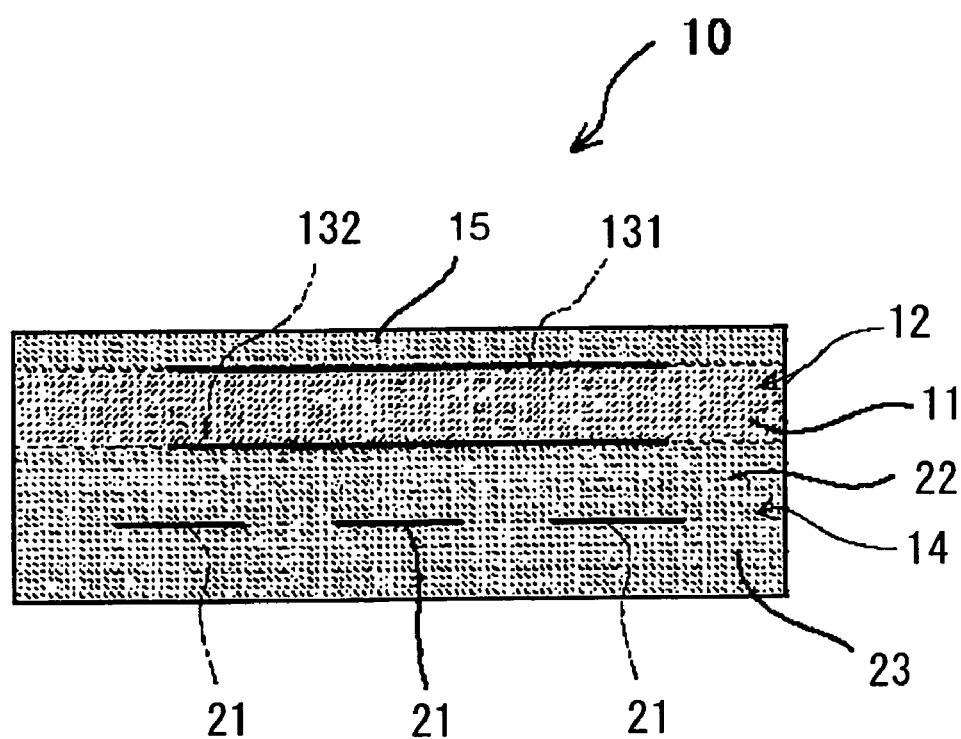
FIG. 1 is cross sectional view of a laminated oxygen sensor element for assembly in a gas sensor (oxygen sensor) according to an embodiment of the invention, the cross section being taken along a direction perpendicular to the longitudinal direction of the sensor element.

Reference numbers used to identify certain structural elements in the drawings including the following.
100 control apparatus
10 laminated-type oxygen sensor element (gas sensor element)
11 solid electrolyte plate
12 detection element
131 detection electrode
132 reference electrode
14 heater
21 heating resistor element
30 gas sensor (oxygen sensor)
32 sensor circuit
34 heater control circuit
36 power-source-voltage detection circuit
38 water temperature senor
42 battery
44 microcomputer

DETAILED DESCRIPTION OF THE PREFERRED EMBODIMENTS

A control apparatus for a gas sensor according to an embodiment of the present invention will now be described with reference to FIGS. 1 to 4. In the present embodiment, the gas sensor is an oxygen sensor for detecting the concentration of oxygen contained in exhaust gas discharged from an internal combustion engine (an engine of an automobile), and a control apparatus 100 equipped with an oxygen sensor will be described hereinbelow. However, the present invention should not be construed as being limited thereto.

Figure 2:
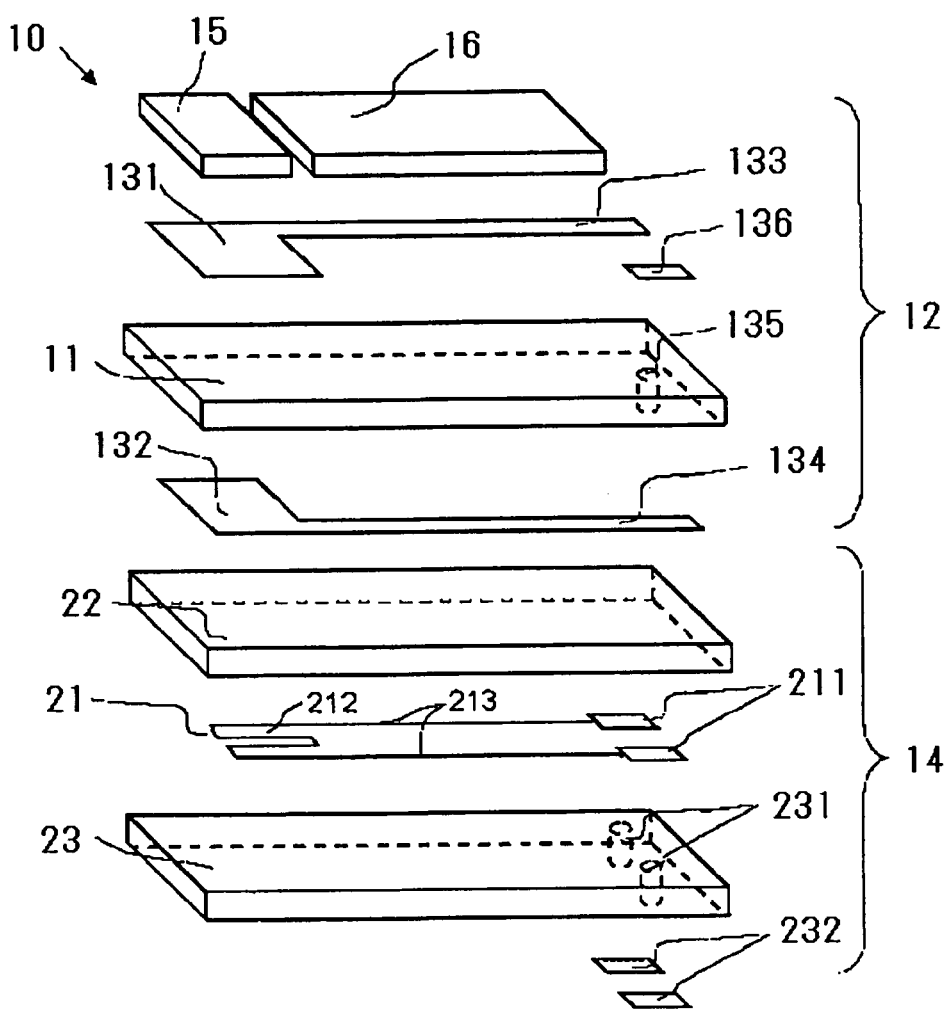
FIG. 2 is an exploded perspective view of the laminated oxygen sensor element according to the embodiment.

As shown in FIGS. 1 and 2, the oxygen sensor used in the control apparatus 100 of the present embodiment includes a laminated-type oxygen sensor element 10 including a detection element 12 and a heater 14, which have been laminated and integrally fired. FIG. 1 shows a transverse cross section (a transverse cross section including a detection element 131, which will be described below) of the laminated-type oxygen sensor element 10 of the present embodiment taken along a direction perpendicular to the longitudinal direction thereof. FIG. 2 is an exploded perspective view showing the structure of the laminated-type oxygen sensor element 10 of FIG. 1. Notably, the laminated-type oxygen sensor element 10 is disposed in the interior of a metallic shell. The oxygen sensor 30 is attached to a predetermined mount portion of an exhaust pipe via the metallic shell, whereby the oxygen sensor 30 is disposed at a predetermined position within the exhaust pipe.

The detection element 12 includes a solid electrolyte plate 11 formed mainly of zirconia. A reference electrode 132 is formed on a surface of the solid electrolyte plate 11, which surface faces the heater 14, and a detection electrode 131 is formed on a surface of the solid electrolyte plate 11, which surface is opposite the reference electrode 132. Conductor lead portions 133 and 134 extend from the detection electrode 131 and the reference electrode 132, respectively, along the longitudinal direction of the solid electrolyte plate 11. A distal end of the conductor lead portion 133 is connected to an external terminal (not shown) to which the sensor circuit is connected. A distal end of the conductor lead portion 134 is connected to a signal output terminal 136 via a through hole 135 extending through the solid electrolyte plate 11. The signal output terminal 136 is connected to an external terminal (not shown) to which a sensor circuit is connected. A porous electrode protecting layer 15 is formed on the detection electrode 131 so as to protect the detection electrode 131 from poisoning. A strengthening-protecting layer 16 is formed on the conductor lead portion 133, excluding a portion to be connected to the external terminal, so as to protect the solid electrolyte plate 11.

The heater 14 includes a heating resistor element 21 formed mainly of platinum, and the heating resistor element 21 is sandwiched between a first substrate 22 and a second substrate 23, which are formed mainly of alumina, which has a high insulating property. In order to locally heat a portion (a so-called gas detection section) of the solid electrolyte plate 11, which section is sandwiched between the detection electrode 131 and the reference electrode 132, the heating resistor element 21 has a heat generation portion 212 formed in a meandering pattern, and a pair of heater lead portions 213, which are connected to the opposite end portions of the heat generation portion 212, respectively, and extend along the longitudinal direction. End portions 211 of the heater lead portions 213 opposite the end portions connected to the heat generation portion 212 are electrically connected to a pair of heater electrification terminals 232 via two through holes 231 extending through the second substrate 23. The heater electrification terminals 232 are connected to corresponding external terminals.

Figure 3:
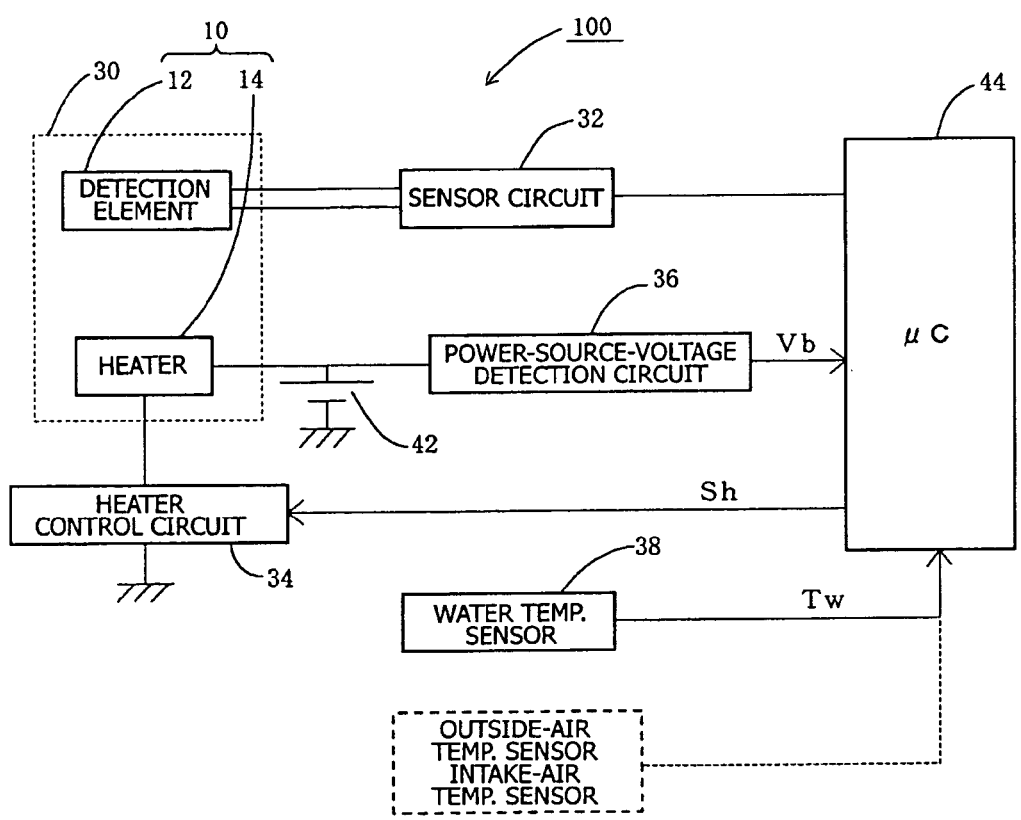
FIG. 3 is a schematic diagram of a control apparatus for the gas sensor (oxygen sensor) according to the embodiment.

Next, the general configuration of the control apparatus 100 equipped with the oxygen sensor 30, in which the above-described laminated-type oxygen sensor element 10 is assembled, will be described with reference to a system diagram shown in FIG. 3. The oxygen sensor 30 includes the laminated-type oxygen sensor element 10 in which the detection element 12 and the heater 14 are laminated as described above. A sensor circuit 32 is connected to the detection element 12 (specifically, to the detection electrode 131 and the reference electrode 132 of the detection element 12). One terminal of the heater 14 (specifically, the heating resistor element 21 of the heater 14) is connected to a battery (on-vehicle power source) 42, and the other terminal of the heater 14 is connected to a heater control circuit 34. In this manner, the heater 14 forms a closed loop in cooperation with the battery 42 and the heater control circuit 34. In the present embodiment, the battery 42 is a lead acid battery having a rated voltage of 12 V.

The sensor circuit 32 and the heater control circuit 34 are connected to a microcomputer 44. Since the sensor circuit 32 and the heater control circuit 34 each have a known circuit configuration, their detailed descriptions are omitted. The heater control circuit 34 is constituted by a switching element (e.g., FET) for pulse-driving the heater 14 on the basis of a pulse signal Sh (described below) output from the microcomputer 44. Although the details are not illustrated, the microcomputer 44 has a known configuration, and includes a microprocessor for performing calculation, RAM for temporarily storing a program and data, ROM for holding the program and data, an A/D converter, an input port, etc.

In addition to the sensor circuit 32 and the heater control circuit 34, a power-source-voltage detection circuit 36 for detecting the voltage Vb of the battery 42 is connected to the microcomputer 44. Further, a water temperature sensor 38, which is exposed to the interior of a water jacket of the engine and detects cooling water temperature Tw, is connected to the microcomputer 44, whereby a signal from the water temperature sensor 38 is input to the microcomputer 44. Notably, the microcomputer 44 has a function (realized by heater electrification processing described below) for calculating a duty ratio of a waveform of voltage applied to the heater 14 (specifically, the heating resistor element 21), on the basis of the voltage Vb of the battery 42 (hereinafter also referred to as battery voltage Vb) and the cooling water temperature Tw. The microcomputer 44 has a PWM port for outputting the pulse signal Sh for effecting PWM control of supply of electricity to the heater 14 in accordance with the calculated duty ratio.

Figure 4:
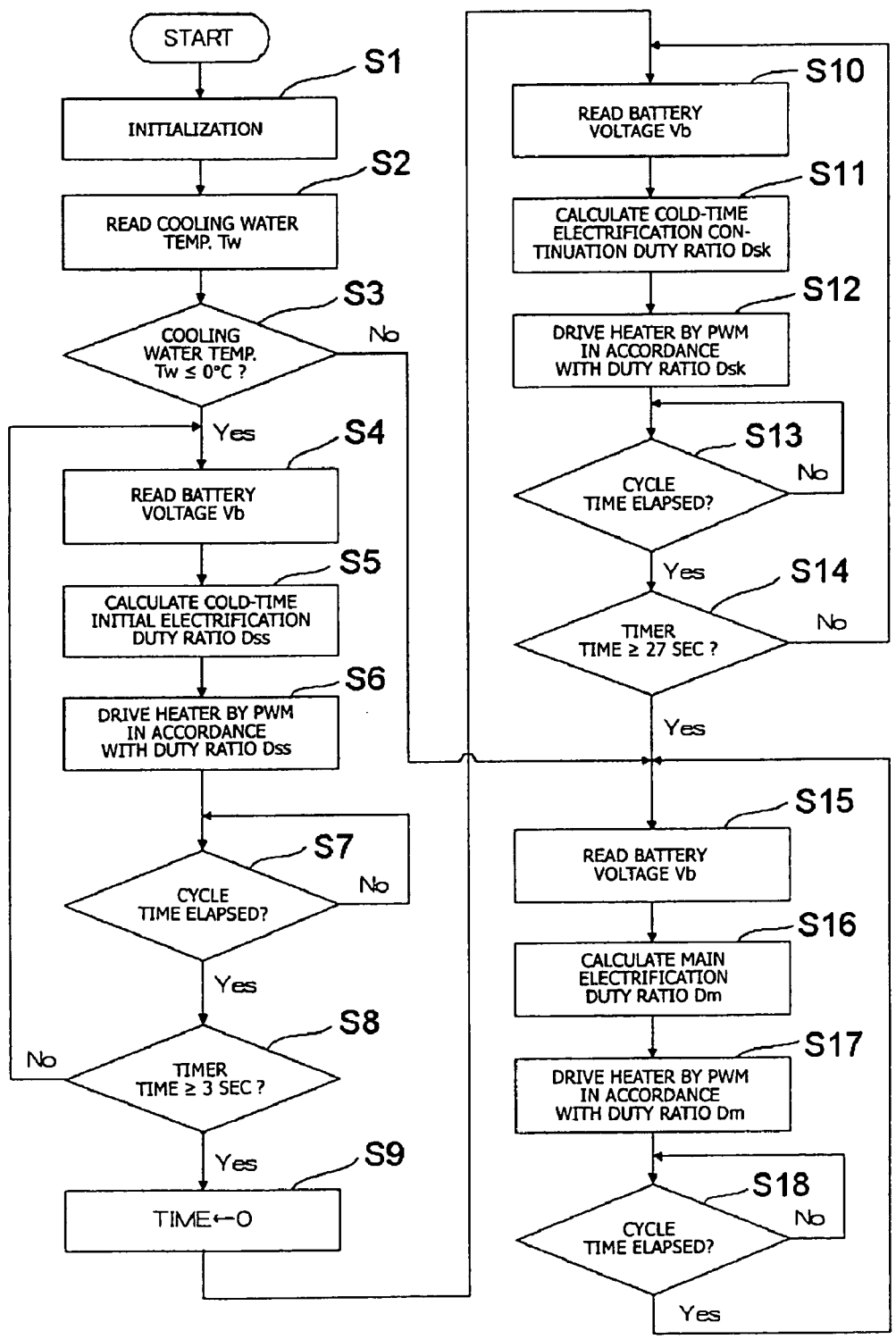
FIG. 4 is a flowchart of heater electrification control (heater control routine) that is executed by the control apparatus of the present embodiment.

Next, heater electrification control (a heat control routine) performed by the microcomputer 44 of the control apparatus 100 of the present embodiment will be described with reference to FIG. 4. When the engine of the automobile is operated, a constant voltage is supplied to the microcomputer 44 via an unillustrated regulator circuit. As a result, a necessary program is read from the ROM, and the heater control circuit 34 is controlled as described below.

First, in step S1, the microcomputer 44 performs an initial setting of the program. During this initial setting, the microcomputer 44 i) initializes a timer variable (TIME=0), ii) sets an initial value LL to be 121 (=$11^2$), which value is used for calculating a main electrification duty ratio Dm during electrical power supply corresponding to 11 V, iii) sets an initial value MM to be 9 (=$3^2$), which value is used for calculating a cold-time electrification continuation duty ratio Dsk during electrical power supply corresponding to 3V, and iv) sets an initial value NN to be 100 (=$10^2$), which value is used for calculating a cold initial electrification duty ratio Dss during electrical power supply corresponding 10 V. This setting is based on electrical power being proportional to the square of voltage.

Then, the microcomputer 44 proceeds to step S2 so as to acquire a signal from the water temperature sensor 38 via the input port to thereby detect the cooling water temperature Tw. Subsequently, in step S3, the microcomputer 44 determines whether the cooling water temperature Tw is 0° C. or lower. When the cooling water temperature Tw is higher than 0° C. (No), the microcomputer 44 determines that condensation water within the exhaust pipe is not generated; i.e., that there is no possibility of occurrence of cracking (splash water cracking) of the detection element 12 resulting from adhering condensation water. In this case, the microcomputer 44 proceeds to step S15.

In the present embodiment, the oxygen sensor 30 is constituted from the detection element 12 having the above-described configuration. In consideration of the thickness, material, etc., of the detection element 12, when condensation water adheres to the surface of the detection element 12 in a state in which it has been heated to about 300° C. or higher, cracking (splash water cracking) may occur in the detection element 12 due to thermal shock. Therefore, when the cooling water temperature Tw is equal to or lower than 0° C. (Yes), the microcomputer 44 determines that condensation water within the exhaust pipe is generated, and proceeds to step S4. In step S4, the microcomputer 44 acquires the battery voltage Vb.

After that, the microcomputer 44 proceeds to step S5 so as to obtain the cold-time initial electrification duty ratio Dss in accordance with the equation "Dss=NN/$Vb^2$." For example, in the case where Vb=12 V, 0.69 (=69%) is obtained as the cold-time initial electrification duty ratio Dss (Dss=100/$12^2$≈0.69). After that, in step S6, the microcomputer 44 outputs from the PWM port the pulse signal Sh which changes in accordance with the obtained cold-time initial electrification duty ratio Dss (e.g., 0.69), to thereby pulse-drive the heater 14 (specifically, the heating resistor element 21) at the cold-time initial electrification duty ratio Dss by use of the heater control circuit 34. Since the heater 14 is pulse-driven at the cold-time initial electrification duty ratio Dss determined from the battery voltage Vb, electrical power is supplied to the heater 14 in an amount equivalent to that where 10 V (DC 10 V) is applied to the heater 14.

Subsequently, in step S7, the microcomputer 44 waits for passage of a predetermined cycle time (e.g., 0.25 sec), and in step S8, the microcomputer 44 determines whether the timer variable TIME satisfies the relation TIME≧3 sec. When the period of 3 sec has not yet passed (No), the microcomputer 44 returns to step S4. When the period of 3 sec has passed (Yes), the microcomputer 44 proceeds to step S9, and initializes the timer variable (TIME=0). With this operation, advance supply of electrical power corresponding to 10 V at the time of cold initial startup ends upon elapse of 3 sec.

Subsequently, the microcomputer 44 proceeds to step S10, and acquires the battery voltage Vb in the same manner as in step S4. After that, the microcomputer 44 proceeds to step S11 so as to obtain the cold-time electrification continuation duty ratio Dsk in accordance with the equation "Dsk=MM/$Vb^2$." For example, in the case where Vb=12 V, 0.06(=6%) is obtained as the cold-time electrification continuation duty ratio Dsk (Dsk=9/$12^2$≈0.06). After that, in step S12, the microcomputer 44 outputs from the PWM port the pulse signal Sh which changes in accordance with the obtained cold-time electrification continuation duty ratio Dsk (e.g., 0.06), to thereby pulse-drive the heater 14 at the cold-time electrification continuation duty ratio Dsk by use of the heater control circuit 34. Since the heater 14 is pulse-driven at the cold-time electrification continuation duty ratio Dsk determined from the battery voltage Vb, electrical power is supplied to the heater 14 in an amount equivalent to that where 3 V (DC 3 V) is applied to the heater 14.

After that, in step S13, the microcomputer 44 waits for passage of a predetermined cycle time (e.g., 0.25 sec), and in step S14, the microcomputer 44 determines whether the timer variable TIME satisfies the relation TIME≧27 sec. When the period of 27 sec has not yet passed (No), the microcomputer 44 returns to step S10. When the period of 27 sec has passed (Yes); i.e., when 30 sec has elapsed after the cooling water temperature had been determined to be equal to or lower than 0° C., the microcomputer 44 proceeds to step S15. Notably, processing of the above-described steps S4 to S14 corresponds to pre-electrification before main electrification is carried out in step S15 and steps subsequent thereto.

In step S15, the microcomputer 44 acquires the battery voltage Vb in the same manner as in steps S4 and S10. After that, in step S16, the microcomputer 44 obtains the main electrification duty ratio Dm in accordance with the equation "Dm=LL/Vb$^2$." For example, in the case where Vb=12 V, 0.84(=84%) is obtained as the main electrification duty ratio Dm (Dm=121/12$^2$≈0.84). After that, in step S16, the microcomputer 44 outputs from the PWM port the pulse signal Sh which changes in accordance with the main electrification duty ratio Dm (e.g., 0.84), to thereby pulse-drive the heater 14 at the main electrification duty ratio Dm by use of the heater control circuit 34. Since the heater 14 is pulse-driven at the main electrification duty ratio Dm determined from the battery voltage Vb, electrical power is supplied to the heater 14 in an amount equivalent to that where 11 V (DC 11 V) is applied to the heater 14.

After that, in step S18, the microcomputer 44 waits for passage of a predetermined cycle time (e.g., 0.25 sec), and then, the microcomputer 44 returns to step S15. After this point in time, electrical power is continuously supplied to the heater 14 in an amount equal to that in the case where DC 11 V is applied to the heater 14, until operation of the automobile (engine) is stopped and operation of the microcomputer 44 is stopped.

Figure 5:
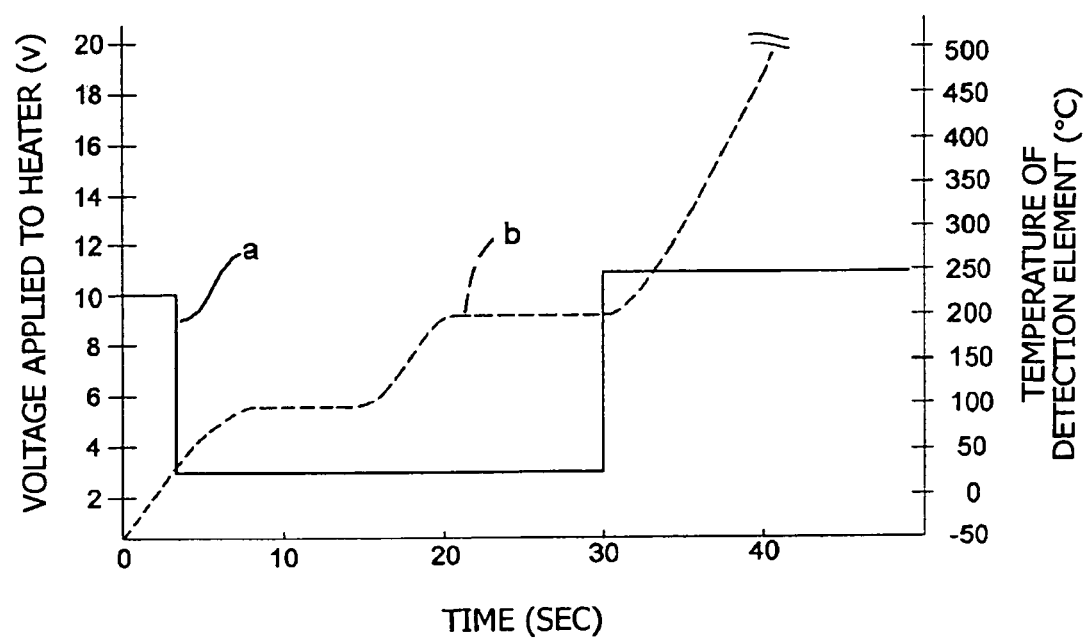
FIG. 5 is a graph which relates to the control apparatus for the gas sensor (oxygen sensor) according to the embodiment, and shows the change in temperature of a detection element as a function of electrical power supplied to the heater, the detection element being laminated on the heater.

Among the heater electrification controls performed by the microcomputer 44, FIG. 5 shows heater electrification control performed when the cooling water temperature Tw is determined to be equal to or lower than 0° C. in step S3, along with behavior of temperature (temperature change) of the detection element 12 at that time. In FIG. 5, line "a" represents the pattern of supply of electrical power to the heater 14 (specifically, the heating resistor element 21), and line "b" represents the temperature change at the detection section of the detection element 12 layered on the heater 14. Notably, in the test, a certain amount of water was caused to adhere to the surface of the detection element 12 before start of electrification, and its temperature was about 0° C. before start of electrification.

Since the above-described heater electrification control is performed by the microcomputer 44, 10-V electrical power is supplied to the heater 14 for 3 sec after startup of the engine, and then 3-V electrical power is supplied to the heater 14 for 27 sec. As a result, the temperature of the heater 14 quickly increases and becomes stable at about 200° C. during the pre-electrification period before elapse of 30 sec. Meanwhile, the temperature of the detection element 12 elevates to follow the temperature rise of the heater 14. However, since water adheres to the surface of the detection element 12, the temperature rise of the detection element 12 temporarily stops at about 100° C. Thus, the temperature of the detection element 12 is maintained at about 100° C. until water adhering to the surface of the detection element 12 evaporates as a result of heating by means of the heater 14. When the water has evaporated, the temperature of the detection element 12 again increases, and becomes stable at about 200° C.

As described above, in the present embodiment, when it is determined that generation of condensation water within the exhaust pipe is expected (i.e., when the cooling water temperature Tw is equal to or less than 0° C.), electrical power is supplied to the heater 14 in such manner that the temperature of the detection element 12 is heated to 100° C. or higher (in the present embodiment, about 200° C.). By virtue of this operation, even when water (condensation water) adheres to the surface of the detection element 12 from the beginning (e.g., cold start), the water adhering to the detection element 12 is caused to evaporate during the above-described pre-electrification. Further, in pre-electrification, electrical power is supplied to the heater 14 in an amount so as to maintain the temperature of the detection element 12 within a range below the splash-water-cracking generation temperature (in the present embodiment, about 300° C. as described above), while rendering the temperature of the detection element 12 equal to or higher than 100° C. (in the present embodiment, the temperature of the detection element 12 is maintained at about 200° C.). Therefore, even when water adhering to the detection element 12 evaporates during pre-electrification, the temperature difference between the detection element 12 and the heater 14 can be suppressed to a small level, whereby generation of condensation water cracking in the detection element 12 during pre-electrification can be prevented.

Moreover, in the present embodiment, since electrical power is supplied to the heater 14 in an amount so as to maintain the temperature of the detection element within a range below the splash-water-cracking generation temperature (about 300° C.) of the laminated-type oxygen sensor element 10 (in the present embodiment, the temperature of the detection element 12 is maintained at about 200° C.), splash water cracking is also suppressed.

Referring back to FIG. 5, when 30 sec has passed from startup of the engine, the mode of supply of electricity to the heater 14 is switched from pre-electrification to main electrification. With this switching, 11-V electrical power is supplied to the heater 14, and the heat generation quantity of the heater 14 increases. As a result, the temperature of the detection element 12 changes and becomes stable at about 800° C. which is a temperature higher than the activation temperature. Thus, the detection element 12 is activated, and the oxygen sensor 30 becomes able to detect oxygen concentration. Notably, it is generally known that in the case of cold start of an internal combustion engine, generation of splash water stops before elapse of 30 sec after startup of the engine. Therefore, in the present embodiment, upon elapse of 30 sec after startup of the engine, the supply of electricity to the heater 14 is switched to main electrification. Notably, the length of the period of pre-electrification is not limited to 30 sec, and may be made longer.

In the control apparatus 100 of the present embodiment, steps S2 and S3 processed within the microcomputer 44 correspond to the function of the "condensation water determination means". Further, steps S6 and S12 correspond to the function of the "pre-electrification means", and step S17 corresponds to the function of the "heater electrification means".

The present invention has been described in accordance with an embodiment thereof. However, needless to say, the present invention is not limited to the embodiment, and may be modified without departing from the scope of the invention.

For example, in the above-described embodiment, the determination as to whether generation of condensation water within the exhaust pipe is expected is performed on the basis of the cooling water temperature Tw detected by means of the water temperature sensor 38. However, the method of determining whether generation of condensation water within the exhaust pipe is expected is not limited thereto. Specifically, as shown by a broken line in FIG. 3, for determining whether generation of condensation water within the exhaust pipe is expected, the microcomputer 44 may take into consideration not only the cooling water temperature Tw detected by means of the water temperature sensor 38, but also information from an outside-air temperature sensor and an intake-air temperature sensor. Alternatively, in place of the water temperature sensor 38, the above-mentioned outside-air temperature sensor or intake-air temperature sensor may be connected to the microcomputer 44 for enabling the above-described determination to be performed on the basis of information from the sensor.

In the above-described embodiment, the oxygen sensor 30 having a laminated, single cell-type oxygen sensor element 10 is described as an exemplary gas sensor. However, the gas sensor is not limited thereto. For example, the control apparatus of the present invention may be configured by use of an oxygen sensor composed of a detection element having the shape of a bottomed cylinder and a bar-shaped heater inserted into the detection element. A universal air-fuel ratio sensor may also be used, configured such that an oxygen ion pump cell and an oxygen concentration measurement cell are layered with a hollow measurement chamber interposed therebetween to thereby form a detection element (a so-called two-cell-type detection element), and a heater is bonded to the detection element. Moreover, the control apparatus of the present invention may be configured by use of a heater-equipped NOx senor or HC sensor.

The present embodiment employs an electrical power supply pattern for supplying 10-V electrical power to the heater 14 for 3 sec and then supplying 3-V electrical power thereto for 27 sec as pre-electrification. However, the electrical power supply pattern is not limited thereto. Other patterns may be freely selected, insofar as the selected pattern enables supply of electrical power to the heater 14 for maintaining the temperature of the detection element 12 within a temperature range of not lower than 100° C. but below the splash-water-cracking generation temperature at or above which cracking is generated in the gas sensor element 12 due to splash of condensation water. For example, a pattern in which 3-V electrical power is always supplied to the heater may be used for pre-electrification, or a pattern in which after start of supply of 10-V electrical power, this power supply is caused to gradually approach the 3-V electrical power supply may be used for pre-electrification. Moreover, the electrical power supply pattern for main electrification is not limited to that employed in the above-described embodiment.

This application is based on Japanese Patent Application Nos. 2004-83737 and 2005-13882 filed Mar. 22, 2004 and Jan. 21, 2005, respectively, incorporated herein by reference in their entirety.

What is claimed is:

1. A control apparatus for a gas sensor, which apparatus is connected to a gas sensor element which includes a detection element capable of detecting a specific gas contained in exhaust gas passing through an exhaust pipe of an internal combustion engine and a heater for heating the detection element, the control apparatus comprising heater electrification means for supplying electricity to the heater such that the detection element is heated to an activation temperature or higher temperature, the control apparatus further comprising:

condensation water determination means for determining whether condensation water within the exhaust pipe is being generated; and pre-electrification means for supplying electricity to the heater, in place of the heater electrification means, when the condensation water determination means determines that condensation water within the exhaust pipe is being generated, the pre-electrification means supplying to the heater electrical power for maintaining the temperature of the detection element within a temperature range of not lower than 100° C. but below a splash-water-cracking generation temperature at or above which the gas sensor element is subject to cracking when splashed with condensation water, wherein the pre-electrification means supplies eletrical power to the heater at a first power level during a predetermined period of time after the condensation water determination means determines that condensation water within the exhaust pipe is being generated, and supplies electrical power to the heater at a second power level lower than the first power level after passage of the predeterined period of time.

2. The control apparatus for a gas sensor according to claim 1, wherein the internal combustion engine is cooled by cooling water, and said condensation water determination means determines whether condensation water within the exhaust pipe is being generated based on temperature of the cooling water.

3. The control apparatus for a gas sensor according to claim 1, wherein the pre-electrification means supplies, to the heater, pulse width modulated electrical power having a voltage waveform from a power source having a power source voltage, and the pre-electrification means calculates, on the basis of the voltage value of the power source, a duty ratio of the voltage waveform applied to the heater, and controls supply of electricity to the heater by pulse width modulation to thereby supply electrical power to the heater at said first and second power levels.

4. The control apparatus for a gas sensor according to claim 1, wherein the gas sensor element comprises a laminate of a plate-shaped detection element and the heater.

5. A control apparatus for a gas sensor, which apparatus is connected to a gas sensor element which includes a detection element capable of detecting a specific gas contained in exhaust gas passing through an exhaust pipe of an internal combustion engine and a heater for heating the detection element, the control apparatus comprising heater electrification means for supplying electricity to the heater such that the detection element is heated to an activation temperature or higher temperature, the control apparatus further comprising;

condensation water determination means for determining whether condensation water within the exhaust pipe is being generated; and pre-electrification means for supplying electricity to the heater, in place of the heater electrification means, when the condensation water determination means determines that condensation water within the exhaust pipe is being generated, the pre-electrification means supplying to the heater electrical power for maintaining the temperature of the detection element within a temperature range of not lower 100° C. but below a splash-water-cracking generation temperature at or above which the gas sensor element is subject to cracking when splashed with condensation water, wherein the gas sensor element comprises a laminate of the detection element and the heater, and the splash-water-cracking generation temperature is set to fall within a range not lower than 250° C. but not higher than 300° C., wherein the detection element is a plate-shaped detection element.

6. The control apparatus for a gas sensor according to claim 5, wherein said gas sensor element has a substantially rectangular cross section.

7. The control apparatus for a gas sensor according to claim 5, wherein said gas sensor element has a substantially rectangular cross section including four corner portions.

* * * * *